(12) United States Patent
Tornambe et al.

(10) Patent No.: US 7,772,006 B2
(45) Date of Patent: Aug. 10, 2010

(54) AGENT DETECTION AND/OR QUANTITATION IN A BIOLOGICAL FLUID

(76) Inventors: Paul Tornambe, 12630 Monte Vista Rd., #104, Poway, CA (US) 92064; Gholam A. Peyman, 10650 W. Tropicana Cir., Sun City, AZ (US) 85351

( * ) Notice: Subject to any disclaimer, the term of this patent is extended or adjusted under 35 U.S.C. 154(b) by 0 days.

(21) Appl. No.: 12/505,052

(22) Filed: Jul. 17, 2009

(65) Prior Publication Data

US 2010/0047914 A1     Feb. 25, 2010

Related U.S. Application Data

(60) Provisional application No. 61/090,713, filed on Aug. 21, 2008.

(51) Int. Cl.
*G01N 33/48*     (2006.01)
*G01N 33/68*     (2006.01)

(52) U.S. Cl. .............................. 436/63; 436/86; 436/164

(58) Field of Classification Search .................. 436/63, 436/86, 164, 169, 178
See application file for complete search history.

(56) References Cited

U.S. PATENT DOCUMENTS

| 6,773,916 | B1 * | 8/2004 | Thiel et al. ................ 435/326 |
| 7,105,496 | B2 * | 9/2006 | Bouck et al. .............. 514/44 R |
| 2006/0189519 | A1 * | 8/2006 | Volz et al. ................... 514/12 |
| 2007/0202558 | A1 | 8/2007 | Fei et al. |

OTHER PUBLICATIONS

Wang et al. (abstract) Yanke Xinjinzhan, vol. 26(3), 2006, pp. 200-202.*

* cited by examiner

*Primary Examiner*—Maureen M Wallenhorst
(74) *Attorney, Agent, or Firm*—Thompson Hine LLP

(57) ABSTRACT

A method of assessing retinal disease in an eye of a patient by rapid, point of care, quantitative detection of cytokine levels is provided.

6 Claims, 2 Drawing Sheets

AGENT DETECTION AND/OR QUANTITATION IN A BIOLOGICAL FLUID

A method for rapid, point of care, qualitative and/or quantitative detection of an agent in a biological fluid withdrawn from a body cavity. In one embodiment, the method detects cytokine levels in ocular anterior chamber fluid for rapid diagnosis or assessment of retinal disease. In one embodiment, the method may be used to monitor efficacy of treatment of a patient with retinal disease.

The method comprises contacting a biological fluid with a detection reagent and assessing an output of a reagent that can qualitatively and/or quantitatively assess agent. In one embodiment, the method further comprises diagnosing and/or assessing a disease based on the reagent output. In one embodiment, the method comprises contacting a sample of anterior chamber fluid with a cytokine detection reagent. In one embodiment, the detection reagent is a chromogen and undergoes a color change in the presence of different agent levels, including a level that indicates a disease. In one embodiment, the detection reagent is an enzyme that catalyzes the production of an indicator, such as a fluorophore or chromogen.

The biological fluid is any fluid found in a mammal. In one embodiment, the biological fluid is a biopsy fluid. Examples of biological fluids include an eye fluid, cerebral spinal fluid (CSF), ascites fluid, synovial fluid, gastric lavage fluid, pericardial fluid, peritoneal fluid, and abscess/ulcer fluid. Examples of eye fluids includes anterior chamber fluid and vitreous fluid.

The agent to be detected is any entity that exhibits physiological or pathophysiological effects. For example, the agent to be detected can be a pathogen such as bacteria, fungi, viruses, etc., as known to a person of ordinary skill in the art. In one embodiment, the agent to be detected is derived from a pathogen, such as a coat protein. The agent to be detected may also be a biomolecule, such as a protein, ribonucleic acid, or deoxyribonucleic acid. In one embodiment, the agent to be detected is a protein that is involved in cell signaling such as a hormone or a cytokine. In one embodiment, the agent to be detected is vascular endothelial growth factor (VEGF).

BRIEF DESCRIPTION OF THE FIGURES

FIG. 3A shows another embodiment of a fluid extraction apparatus.

Figure 1A:
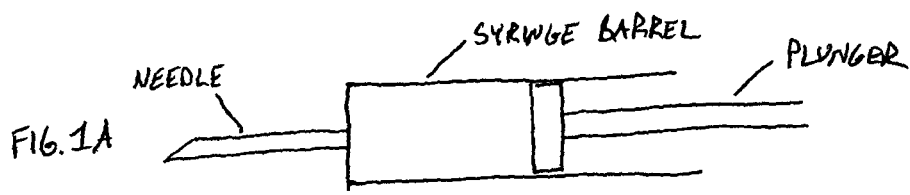
FIG. 1A shows a syringe may be used to draw the biological fluid through the needle into a barrel.
Figure 1B:
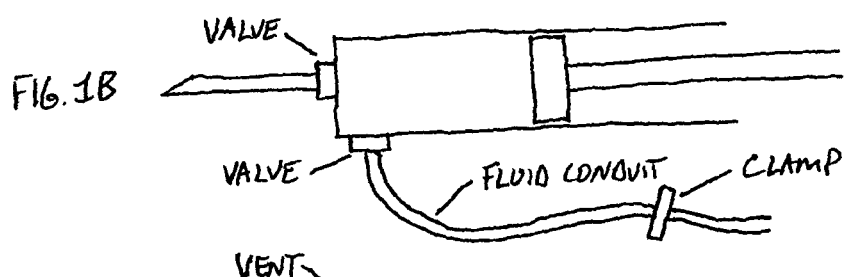
FIG. 1B shows an embodiment with a needle attached to a syringe via a one-way valve.
Figure 1C:
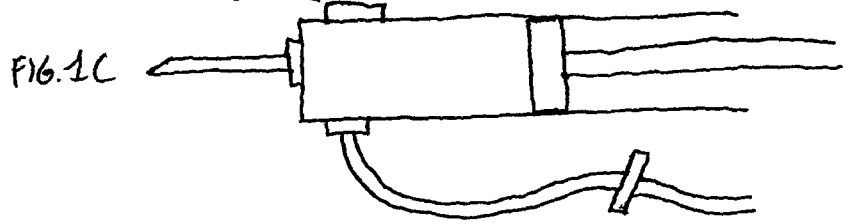
FIG. 1C shows an embodiment with a syringe barrel vented to atmosphere.

In one embodiment, the biological fluid is obtained by any method known to a person of ordinary skill in the art. In one embodiment, a fluid extraction apparatus comprising a syringe is used to obtain the biological fluid. In one embodiment, a needle is attached to a fluid extraction apparatus such as a syringe barrel or other holder for collecting biological fluid through the needle, as shown in FIG. 1A. For example, a syringe may be used to draw the biological fluid through the needle into a barrel. In one embodiment, the syringe draws the fluid by a vacuum using, for example, a plunger or bulb, as known to a person of ordinary skill in the art. In one embodiment, the needle is attached to a syringe via a one-way valve, as shown in FIG. 1B, which only allows fluid flow into the syringe barrel. In one embodiment, a fluid conduit, such as a tube, is attached to the barrel of the syringe at a point of attachment different from the needle, as shown in FIG. 1B. In one embodiment, the fluid conduit is attached to the syringe barrel via a one-way valve, which only allows fluid flow into the syringe barrel. Additionally, the fluid conduit may have at least one additional feature, such as a valve, along the length of the fluid conduit, as shown in FIG. 1B. Examples of valves include one-way and/or multi-way luer stopcock valves. In one embodiment, the valve along the length of the fluid conduit is a clamp. In one embodiment, the syringe barrel is vented to atmosphere, as shown in FIG. 1C. In one embodiment, the vent is a one-way valve that only allows fluid flow out of the syringe barrel. Additionally, the vent may be connected to a fluid conduit such as a tube. The spatial relationship on the syringe barrel between the inward-flowing fluid conduit and the outward-flowing vent may be such that they are on opposite sides of the syringe barrel, as shown in FIG. 1C, or on the same side. In one embodiment, the inward-flowing fluid conduit and the outward-flowing vent are present on the same side of the syringe barrel with the inward-flowing fluid conduit being closer to the needle attachment point. Various fluid extraction apparatus embodiments, as described herein, may be used in the method.

In one embodiment, the biological fluid is anterior chamber fluid and is obtained by accessing the anterior chamber of the eye with a needle having a gauge ranging from about #20 to about #41. In one embodiment, the needle has a gauge ranging from about #30 to about #33. In one embodiment, the needle comprises a stop which prevents undesirable penetration of the needle into the anterior chamber of the eye. In one embodiment, the stop is positioned such that the needle penetrates from about 0.5 mm to about 5.0 mm. In one embodiment, the stop is positioned such that the needle penetrates from about 0.75 mm to about 2.0 mm. In one embodiment, about 0.1 ml of anterior chamber fluid is obtained.

The extracted biological fluid is contacted with an agent detection reagent. In one embodiment, the detection reagent is in the syringe used to withdraw anterior chamber fluid. In one embodiment, the agent detection reagent is a component of the fluid extraction apparatus. For example, the agent detection reagent may be within the barrel of the syringe. In one embodiment, the detection reagent is present, for example, at the proximal end of the barrel of the syringe. In one embodiment, the detection reagent is adhered to or associated with the plunger of the syringe.

In one embodiment, as described above, the fluid extraction apparatus includes a syringe barrel comprising a needle attached via a one-way inward valve, a fluid conduit attached to the barrel via a one-way inward valve, and a vent comprising a one-way outward valve. In one embodiment, the fluid conduit and/or vent allows for the introduction and/or extrusion of a substance such as a liquid or a gas. In one embodiment, the fluid conduit and/or vent allows for venting of the system to the environment. In one embodiment, the fluid conduit and/or vent allows for the introduction and/or extrusion of a solution used in the detection of the agent by the detection reagent. For example, various washes and/or ancillary detection reagents, including antibody and enzyme-substrate solutions, as known to a person of ordinary skill in the art, are introduced and/or extruded via the fluid conduit and/ or vent. In one embodiment, the biological fluid is anterior chamber fluid and the agent is a cytokine.

Figure 2:
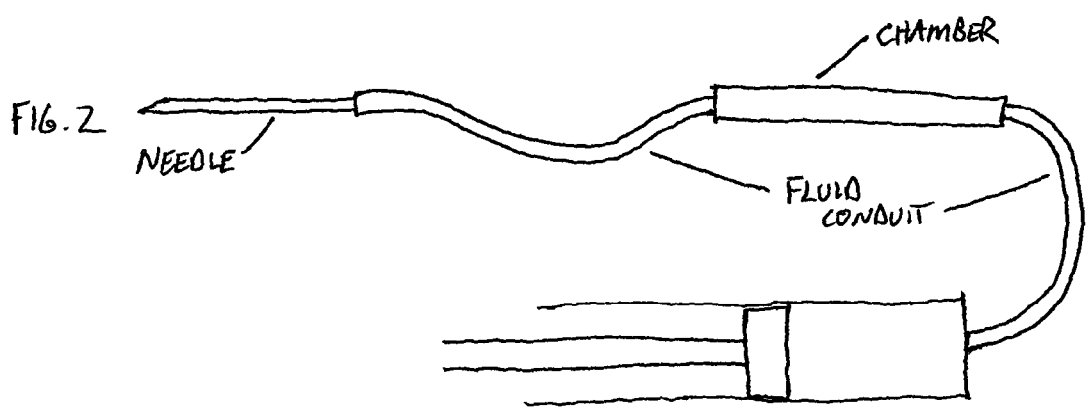
FIG. 2 shows an embodiment with a detection reagent present in a chamber that is in fluid contact with the needle and the syringe barrel via a conduit.

In one embodiment, the needle and the syringe barrel are connected via a fluid conduit such as a tube. In one embodiment, the detection reagent is present in a chamber that is in fluid contact with the needle and the syringe barrel via a conduit, as shown in FIG. 2. In one embodiment, the chamber is a capillary tube. As described, the conduit can have additional features, located either proximal or distal or both, to the chamber.

In one embodiment, the detection reagent is on a solid support for contact with the biological fluid in any of the disclosed configurations. Examples of solid supports include glass, plastic, and various polymers, and may be in various configurations such as beads, rods, sheets, circles, etc. The detection reagent can be coated onto the solid support or incorporated within the solid support. In one embodiment, the solid support is a surface of the fluid extraction apparatus, such as the interior walls of the syringe barrel or the interior walls of a capillary tube. In one embodiment, the solid support containing the detection reagent is inside the barrel of a syringe that is used to withdraw the biological fluid. In one embodiment, the solid support containing the detection reagent is in a chamber, such as a capillary tube, and the biological fluid is contacted with the solid support. In one embodiment, the solid support containing the detection reagent is attached to the plunger of a syringe, such as the fluid extraction apparatus described herein. In one embodiment, the solid support is a slide and is attached to the plunger. In one embodiment, the slide is removably attached to the plunger via a clip that allows the slide to be released from the plunger. In one embodiment, slides containing different detection reagents may be interchangeably attached to a plunger of the fluid extraction apparatus, thus allowing detection of more than one agent. In one embodiment, the agent is nonspecifically associated with the solid support.

In one embodiment, following withdrawal of the biological fluid into the syringe and/or chamber, and contact with the detection reagent, the fluid is extruded and at least one additional solution is taken up into the syringe barrel. In one embodiment, less than all of the biological fluid is extruded prior to an additional solution being taken up into the syringe barrel. In one embodiment, the additional solution is a wash solution or a solution that facilitates agent detection. For example, the additional solution may contain secondary antibodies specific for the agent of interest, conjugated to a detection moiety such as an enzyme. In one embodiment, an additional solution comprises a substrate for an enzyme that catalyzes the production of an indicator, such as a chromogen. In one embodiment, following generation of an indicator by a detection reagent, the indicator is used to determine the concentration of the agent. In one embodiment, the biological fluid is anterior chamber fluid and the agent is a cytokine.

Figure 3A:
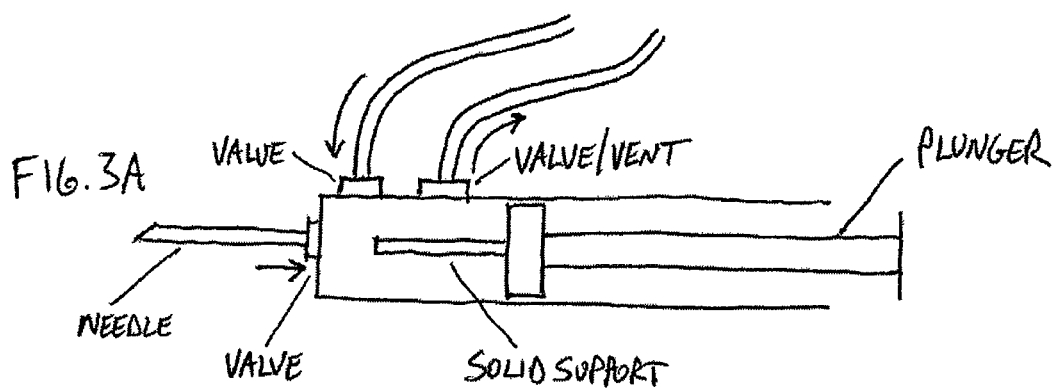
FIG. 3A shows one embodiment of a fluid extraction apparatus.
Figure 3B:
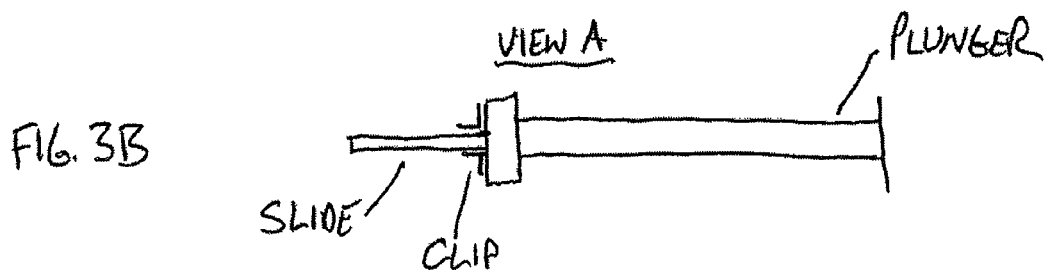
FIG. 3B shows another embodiment of a fluid extraction apparatus.
Figure 3C:
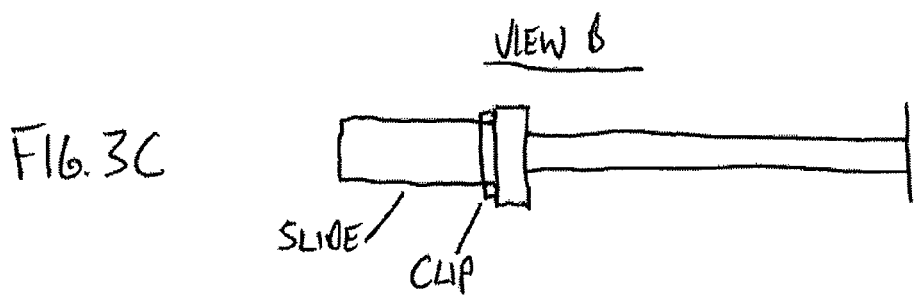

In one embodiment, as shown in FIG. 3A, the fluid extraction apparatus comprises a syringe barrel with a needle attached via an inward one-way valve; a fluid conduit attached to the syringe barrel via a inward one-way valve; distally from the fluid conduit, an outward one-way valve vent which may optionally comprise a fluid conduit; and a detection reagent on a solid support that is attached to the fluid-contacting surface of the plunger, as shown in FIG. 3A. In one embodiment, the solid support is a slide, as shown in FIGS. 3B and 3C. In one embodiment, the fluid extraction apparatus is used in the method as follows:

(a) inserting the needle into a cavity containing a biological fluid of interest;

(b) moving the plunger distally within the syringe barrel, creating negative pressure and causing the inflow of the biological fluid through the inward one-way valve;

(c) moving the plunger proximally within the syringe barrel, causing extrusion of any air in the syringe barrel out the outward one-way valve, and causing the slide containing the detection reagent, which is attached to the plunger, to contact the biological fluid;

(d) after allowing a period of time sufficient for the agent in the biological fluid to interact with the detection reagent on the slide, extruding at least a portion of the barrel contents via the vent by moving the plunger proximally;

(e) introducing fluid via the inward one-way valve by moving the plunger distally, the fluid being a wash or a component of the detection reagent such as a secondary antibody or an enzyme substrate;

(f) after allowing a period of time sufficient for washing and/or incubating the detection reagent, continue introducing and extruding solutions as needed for a particular detection format and generation of an indicator;

(h) determining the amount of indicator on the slide with a suitable instrument or visually.

In one embodiment, steps (a)-(h) are conducted using anterior chamber fluid and the detection of a cytokine, such as VEGF.

In one embodiment, the agent detection reagent is separate from the fluid extraction apparatus, such that the extracted biological fluid is brought into contact with the detection reagent. In one embodiment, the detection reagent is present, for example, in a separate container. In one embodiment, the detection reagent is present, for example, on a surface such as a well, slide, or another surface or container, (e.g., a glass slide, plastic microwell plate, etc.) and the biological fluid is contacted with the detection reagent. In one embodiment, the detection reagent is on any surface on which biological fluid is placed. In one embodiment, the detection reagent is either a solution or a component of a solid matrix. As known to a person of ordinary skill in the art, detection formats that can be employed in the method, include, but are not limited to test strips, dot blots, enzyme-linked immunosorbent assay (ELISA), solutions on slides, etc. In one embodiment, the biological fluid is anterior chamber fluid and the detection reagent detects a cytokine, such as VEGF.

ELISA generally involves at least one antibody with specificity for a particular antigen. U.S. Publication No. 20070202558 discloses the use of ELISA in detecting and/or quantitating VEGF concentration in blood, which is hereby incorporated by reference herein in its entirety. In one embodiment, the biological fluid with an unknown quantity of agent is immobilized on a solid support, either non-specifically, for example, via adsorption to the surface, or specifically, for example, via capture by another antibody specific to the same cytokine, in a sandwich ELISA. After the agent is immobilized, the detection reagent is added, forming a complex with the agent. In one embodiment, the detection reagent is an antibody covalently linked to an enzyme. In another embodiment, the detection reagent is a secondary antibody which is linked to an enzyme, which recognizes a first antibody bound to the agent. Generally, after each ELISA step, a wash is used to remove any proteins or antibodies that are not specifically bound. In one embodiment, after the final wash step, the complex is developed by adding an enzymatic substrate to produce an indicator, such as a visible signal, which indicates the quantity of agent in the sample. In one embodiment, the enzymatic substrate is a chromogenic or fluorogenic.

Examples of detection reagents include reagents that may be detected directly, such as fluorochrome, chemiluminescent, and chromogenic labels, as well as reagents, such as enzymes, that require a substrate to be detected. Examples of such labels include fluorophores such as fluorescein and its derivatives, rhodamine and its derivatives; and enzymes such as luceriferases, horseradish peroxidase (HRP), alkaline phosphatase, and β-galactosidase. In one embodiment, the detection reagent includes a binding moiety, such as an antibody or biotin.

In one embodiment, the detection reagent generates an indicator. Where the indicator is detected optically, detection may be accomplished using any optical detector that is compatible with the spectroscopic properties of the signal. The indicator may involve an increase in an optical signal or a decrease. The optical signal may be based on any optical principal, including fluorescence, chemiluminescence, and light absorbance. In one embodiment, the optical signal to be detected will involve absorbance or emission of light having a wavelength between about 180 nm (ultraviolet) and about 50 μm (far infrared). In one embodiment, the wavelength is between about 200 nm (ultraviolet) and about 800 nm (near infrared). A variety of detection apparatus for measuring light having such wavelengths are known in the art, and typically involve the use of light filters, photomultipliers, diode-based detectors, and/or charge-coupled detectors (CCD), for example.

In one embodiment, the detection reagent generates an indicator in the presence of the desired agent. In one embodiment, the detection reagent is a chromogen and the generation of the indicator, for example a color change of the detection reagent, is based on the concentration of the agent present in the biological fluid. The indicator generated by the detection reagent can be any readily readable output indicating the presence of the agent and/or a clinically relevant concentration of an agent, as known to a person of ordinary skill in the art. In one embodiment, the indicator is a color change in the detection reagent. In one embodiment, the intensity of the color, measured for example as optical density (OD), correlates with the quantity of agent present in the biological fluid.

In one embodiment, the indicator is the generation of a signal, for example, a line on a test strip, that can be read visually unaided. In one embodiment, a biological fluid sample is applied to a test strip and a signal is generated that can be employed to quantitate the agent level in the sample. The indicator producing system may also include an enzyme that catalyzes the conversion of a dye substrate into a detectable product in the presence of an agent, where the amount of indicator that is produced by this reaction is proportional to the amount of agent that is present. In one embodiment, this enzyme is a peroxidase, such as horseradish peroxidase (HRP) and recombinantly produced peroxidase. The dye substrates are oxidized by hydrogen peroxide in the presence of the peroxidase to produce a product that absorbs light in a predetermined wavelength range, i.e., an indicator dye. The amount of light absorbed at the wavelength correlates to the amount of agent present in the sample.

The operating characteristics of the detection reagent, for example the detection ranges, can be selected such that detection and subsequent generation of an indicator indicates a clinically relevant amount of the cytokine in the biological fluid. In one embodiment, the sensitivity of the method is modified such that a positive reading occurs at a clinically relevant agent concentration. In one embodiment, the sensitivity of the method can be calibrated to produce a positive signal by using a known agent concentration. In one embodiment, cytokine levels that exceed a specific level, for example, about 120 pg/ml to about 400 pg/ml, indicate the presence of retinal disease. In one embodiment, a positive reading, such as a color change in the detection reagent, indicates cytokine levels of above about 120 pg/ml to about 400 pg/ml, and thus is diagnostic of retinal disease in the patient. In one embodiment, generation of an indicator resulting from an anterior chamber fluid sample is compared to a standard curve generated from known concentrations of the analyzed cytokine to determine the cytokine concentration in the anterior chamber fluid sample.

In use, the method can assess whether immediate treatment of retinal disease is needed and/or warranted. In one embodiment, the method is performed in a clinical setting, such as a physicians office. Increased cytokine levels, such as VEGF, are present in many ocular diseases Drugs are available that inhibit VEGF and other cytokines. Presently, treatment using VEGF inhibitors (VEGF-I) are based upon indirect evidence of VEGF expression, such as fluorescein angiography, optical coherence tomography, or clinical trials. To date, there is no known rapid, point of care test to measure VEGF levels to determine the need for VEGF-I administration. In one embodiment, the detection reagent detects VEGF, including naturally occurring variants such as splice variants. In one embodiment, the detection reagent generates an indicator, such as a chromogen or fluorogen, in the presence of VEGF. In one embodiment, the detection reagent generates an indicator, such as a chromogenic or fluorogenic moiety, in the presence of VEGF at a concentration of between about 120 pg/ml to about 400 pg/ml, or higher. In one embodiment, the generation of an indicator, such as a chromogen or fluorogen, indicates presence of a retinal disease. In one embodiment, the level of the generated indicator is quantitated, for example, by measuring the optical properties of the analyzed sample following incubation of the anterior chamber fluid with a detection reagent. In one embodiment, the quantitated indicator level is compared to a stand curve generated using the same detection reagent and known cytokine concentrations. As used herein, a patient refers to mammals, including humans.

In embodiments, the method detects levels of cytokines that include, but are not limited to, VEGF, interleukin-4 (IL-4), interleuken-13 (IL-13), interferon gamma (IFNγ), interleuken-6 (IL-6), and/or interleuken-8 (IL-8), including naturally occuring variants. The method may detect a cytokine in the presence of at least one additional physiologically relevant component. The method may also comprise more than one detection reagent.

When clinically relevant levels of at least one cytokine are detected, a diagnosis of retinal disease may be made and the patient then considered for immediate treatment. In one embodiment, VEGF or other cytokine inhibitors, including but not limited to cortisone, tumor necrosis factor inhibitors, or other inhibitors of cytokines or inflammation, may be administered to the patient.

In one embodiment, a kit comprises the described fluid extraction apparatus and at least one component of the detection reagent, such as a primary and/or secondary antibody, a solid support, or an enzyme substrate. In one embodiment, the detection reagent, or a component, is associated with a solid support. As described, the fluid extraction apparatus can include a needle, a syringe, and/or a conduit, which may further include at least one additional feature.

The method will be further appreciated with respect to the following example.

The VEGF concentrations in ocular anterior chamber fluid were compared in a group of 40 patients either diagnosed with retinal diseases (test) or exhibiting no retinal disease (control). The test group had retinal diseases including exudative macular degeneration, proliferative diabetic retinopathy, diabetic macular edema, retinal vascular occlusions, retinal detachment, and other diseases of the eye which caused neovascularization of the retina or choroid. Changes in the levels of VEGF in the anterior chamber fluid between the two groups were compared.

The anterior chamber fluid from the two groups was analyzed for levels of VEGF using ELISA. All of the test patients with retinal disease had anterior chamber fluid VEGF concentrations of about 120 pg/ml to about 400 pg/ml or higher. None of the control patents had VEGF levels that exceeded 120 pg/ml.

Other variations or embodiments will also be apparent to a person of ordinary skill in the art from the above description and example. Thus, the forgoing embodiments are not to be construed as limiting the scope of this invention.

What is claimed is:

1. A method of rapidly diagnosing retinal disease by quantitative detection of cytokine levels in an eye of a patient, comprising:
   (a) contacting ocular anterior chamber fluid from a patient with a detection reagent that detects a clinically relevant concentration of a single cytokine in the ocular anterior chamber fluid by generating an output as a result of an interaction between the single cytokine in the ocular anterior chamber fluid and the detection reagent,
   (b) assessing the output of the detection reagent, and
   (c) diagnosing the presence of a retinal disease based on the output of the detection reagent,
wherein quantitative detection of the clinically relevant concentration in the ocular anterior chamber fluid of the patient results in rapid diagnosis of a retinal disease.

2. The method of claim 1 wherein the clinically relevant concentration of the cytokine is about 120 pg/ml to about 400 pg/ml, and indicates the presence of retinal disease.

3. The method of claim 1 wherein the single cytokine is vascular endothelial growth factor (VEGF).

4. A method of rapidly diagnosing retinal disease by quantitative detection of cytokine levels in an eye of a patient, comprising:
   (a) contacting ocular anterior chamber fluid from a patient with a detection reagent that detects a clinically relevant concentration of a cytokine in the ocular anterior chamber fluid by generating an output as a result of an interaction between the cytokine in the ocular anterior chamber fluid and the detection reagent,
   (b) assessing the output of the detection reagent, and
   (c) diagnosing the presence of a retinal disease based on the output of the detection reagent,
wherein quantitative detection of the clinically relevant concentration in the ocular anterior chamber fluid of the patient results in rapid diagnosis of a retinal disease, and wherein the detection of a clinically relevant concentration of a single cytokine results in rapid diagnosis of a retinal disease.

5. The method of claim 4 wherein the clinically relevant concentration of the cytokine is about 120 pg/ml to about 400 pg/ml, and indicates the presence of retinal disease.

6. The method of claim 4 wherein the single cytokine is vascular endothelial growth factor (VEGF).

* * * * *